United States Patent [19]

Rand

[11] Patent Number: 4,638,803

[45] Date of Patent: Jan. 27, 1987

[54] MEDICAL APPARATUS FOR INDUCING SCAR TISSUE FORMATION IN A BODY

[76] Inventor: Robert W. Rand, 521 N. Bristol St., Los Angeles, Calif. 90049

[21] Appl. No.: 677,601

[22] Filed: Nov. 30, 1984

Related U.S. Application Data

[63] Continuation of Ser. No. 429,088, Sep. 30, 1982, abandoned.

[51] Int. Cl.$^4$ ............................................. A61B 17/12
[52] U.S. Cl. ................................... 128/325; 604/175; 623/11
[58] Field of Search .................... 604/96–100, 604/103, 175, 282; 128/325, 344, 1 R; 623/7, 11, 12, 1

[56] References Cited

U.S. PATENT DOCUMENTS

| | | | |
|---|---|---|---|
| 3,598,126 | 8/1971 | Hoeltzenbein | 604/282 |
| 4,085,757 | 4/1978 | Pevsner | 604/96 |
| 4,213,461 | 7/1980 | Pevsner | 604/96 |
| 4,282,875 | 8/1981 | Serbinenko | 128/325 |
| 4,327,734 | 5/1982 | White, Jr. | 128/325 |
| 4,341,218 | 7/1982 | Ü | 604/97 |
| 4,364,392 | 12/1982 | Strother et al. | 604/98 |

FOREIGN PATENT DOCUMENTS 0810246  3/1981  U.S.S.R. ................................ 604/96

OTHER PUBLICATIONS

"New Products and Processes" (B-D Mini-Balloons) *Polymer News*, vol. 7, No. 5 (May 1981) p. 219.

Serbinenko, F. A., "Balloon Catheterization and Occlusion of Major Cerebral Vessels", *J. Neurosurg.*, vol. 41, pp. 125–145 (Aug. 1974).

"Stereotaxy of the Human Brain", edited by Schaltenbrand and Walker et al., Theime-Stratton, Inc. N.Y. 1982, p. 674.

"Biosurface Chemistry for Fun and Profit", Chemtech, vol. 16, No. 3 (Mar. 1986), p. 178, Robert E. Baier and Anne E. Meyer.

*Primary Examiner*—Michael H. Thaler
*Attorney, Agent, or Firm*—Herb Boswell

[57] ABSTRACT

An inflatable balloon capable of being delivered to a site within a body via a catheter or the like, includes on its surface a composition. The composition is capable of inducing the formation of a thrombosis followed by invasion of capillaries and fibroblasts to the thrombosis and subsequent scar formation. Scar formation fixedly adheres the balloon at its placement site to permanently locate the balloon at this placement site.

14 Claims, 3 Drawing Figures

U.S. Patent  Jan. 27, 1987  4,638,803
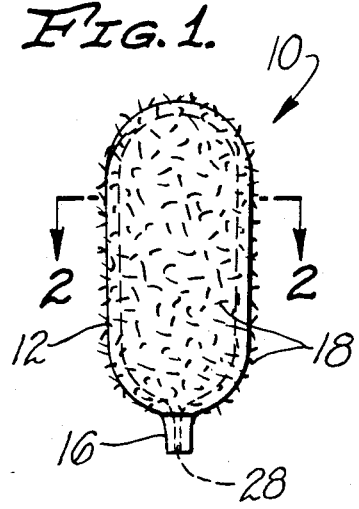
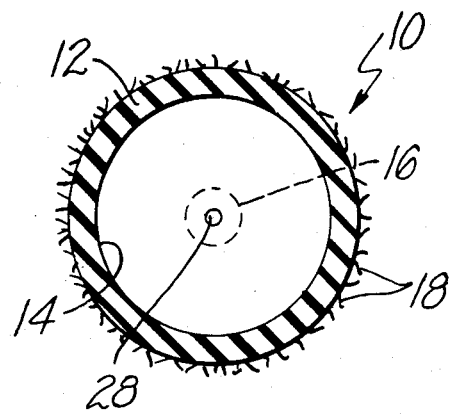
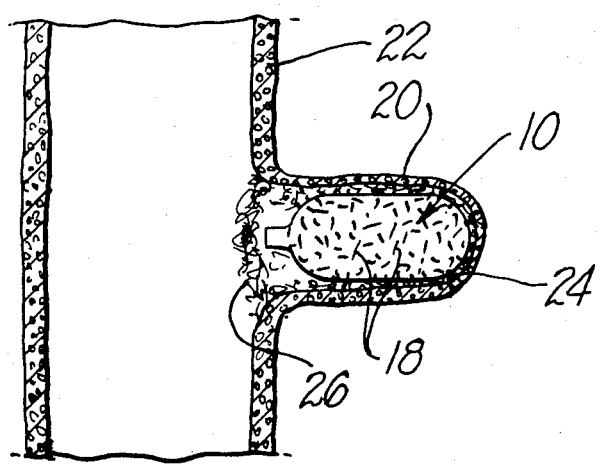

MEDICAL APPARATUS FOR INDUCING SCAR TISSUE FORMATION IN A BODY

This is a continuation, of application Ser. No. 429,088, filed Sept. 30, 1982, now abandoned.

BACKGROUND OF THE INVENTION

This invention is directed to an apparatus and a process in utilizing that apparatus whereby a composition is located on the surface of the apparatus such that, upon introduction of the apparatus within a site in a body, the composition induces thrombosis followed by capillary and fibroblast infiltration and subsequent scar formation to fixedly hold the apparatus in position within the body.

In a paper entitled, "Ferromagnetic Silicone Vascular Occlusion In A Superconducting Magnetic Field Preliminary Report" *Bulletin of the Los Angeles Neurological Societies,* Vol. 37, No. 2, April, 1972, 67, I, along with my co-author, described a technique of arterial occlusion with silicone emboli as a means for treating unresectable angiomatous neoplasms. In that paper, we described the use of iron microspheres as a means of attempting to hold a vulcanizing silicone mass in position within an artery. A superconducting electromagnet was utilized to hold the iron shperes in a fixed position within the artery after introduction of the iron spheres and the components of the vulcanizing mass via a catheter. The iron spheres, in turn, were utilized to hold the vulcanizing mass in position until vulcanization was complete and a fixed body was formed within the artery.

This technique was extended to the treatment of cerebral aneurysms as was reported by me and the same co-author in "Treatment of Cerbral Aneurysms by Stereotaxic Ferromagnetic Silicone Thrombosis," *Bulletin of the Los Angeles Neurological Societies,* Vol. 38, No. 1, January, 1973, 21. The technique was further extended to infarction at a portion of an organ as reported in my and my co-author's paper entitled, "Ferromagnetic Silicone Vascular Occlusion: A Technique for Selective Infarction of Tumors and Organs", *Annals of Surgery,* Vol. 178, No. 5, November, 1973, 663.

As an improvement over the technique utilizing the external magnet to position the vulcanizing agent having iron particles suspended therein, a technique was later developed wherein a magnetic stereotaxic probe, which was shaped as a cylindrical magnet allowing for insertion of a long, thin needle through the center, was constructed. The magnet was of sufficient strength such that iron particles suspended in components capable of vulcanizing into an intact body, was introduced into an aneurysm or the like, by passing these components through the needle placed through the center of the magnet. The tip of the magnet was maintained in contact with the outside of the aneurysm or the like to maintain the position of the iron particles, and thus the vulcanized mass surrounding them, within the aneurysm for a period of time. Upon introduction of a metallic thrombosis, the magnet was removed, leaving a vulcanized mass including the iron particles therein to fill up the aneurysm and thus lessen the chances of rupture of the same with an accompanying hemorrhage. This work is reported in "Stereotaxy of the Human Brain", Edited by Schaltenbrand, G. and Walker, A. E., et al, Theime-Stratton, Inc., New York, 1982, page 674.

The use of balloons to temporarily or permanently occlude a vessel or the like was originally pioneered by Serbinenko, *Journal of Neurosurgery,* 41:125-145, 1974. Along with several co-authors in, "Development of Detachable Vascular Balloon Catheter", *Bulletin of the Los Angeles Neurological Societies,* Vol. 41, No. 1, January, 1976, 2, I describe the intercranial use of balloons for the occlusion of a vessel in an experimental animal. Further, in the article entitled, "Stereotaxy of the Human Brain" (op. cit.), further work with regard to the use of these balloons is described. The deflated balloon is inserted utilizing a catheter in an appropriate vessel or artery. Once in position, the balloon is inflated and techniques are available for detaching the balloon from the catheter, allowing withdrawal of the catheter once the balloon is inflated and is in position. The procedures of so utilizing balloons as described in these articles are herein incorporated by reference.

As is noted in my article described above, entitled, "Stereotaxy of the Human Brain", the presence of iron particles within the body results in the formation of a metallic thrombus. As noted in that article, this thrombus can then serve to seal or eliminate an aneurysm from the circulation.

BRIEF DESCRIPTION OF THE INVENTION

In view of the above, it is a broad object of this invention to permanently affix a medical appliance or the like within a body by utilizing the metallic thrombosis reaction to cause interaction between the body and the appliance, such that scar tissue will form around the appliance to fixedly hold the appliance within the body. It is a further object of this invention to utilize this mechanism to fixedly hold medical balloons in position in a body. It is an additional object to utilize the metallic thrombosis reaction to fixedly hold a medical balloon within a vessel, artery, fistula or aneurysm within a body to seal said vessel, artery, fistula or aneurysm.

These and other objects, as will become evident from the remainder of this application are achieved in a process of adhering a medical apparatus within a human body which comprises: incorporated onto the surface of said apparatus a composition having the property of inducing the formation of thrombosis followed by capillary and fibroblast invasion of the thrombosis and subsequent scar tissue formation; locating said apparatus in a position within said body for a period of time sufficient such that said composition induces said formation of said thrombosis and said capillary and fibroblast invasion and subsequent scar tissue formation in an area within said body adjacent to said position of said apparatus.

These and other objects, as will also become evident from the remainder of this specification, are additionally achieved in a medical balloon which comprises: an inflatable balloon formed from an elastomeric material; a composition present on at least the surface of said balloon, said composition of a type capable of inducing the formation of thrombosis followed by invasion of capillaries and fibroblasts and subsequent scar tissue formation.

The preferred composition for causing the thrombosis, capillary and fibroblast invasion and scar tissue formation would be chosen from the group consisting of iron, copper, tantalium, gold, silver and platinum. A more preferred group would be iron, copper or tantalum. An even more preferred group would be iron and copper with iron forming the preferred composition as presently used.

The balloon would be preferably formed of an elastomeric material such as a latex, or silicone elastomer. Preferredly, the balloon would be of the type capable of being inserted in the body by utilization of a catheter and detached from the catheter, inflated and left in the body upon withdrawal of the catheter.

BRIEF DESCRIPTION OF THE DRAWINGS

The invention described in this specification will be better understood when taken in conjunction with the drawings wherein:

FIG. 1 is an elevational view of a medical balloon as utilized in this invention;

FIG. 2 is a sectional view about the lines 2—2 of FIG. 1;

FIG. 3 is a hypothetical representational view showing use of a balloon prepared and used as per this invention as located in an arterial aneurysm.

The invention described in this specification utilizes certain principles and/or concepts as are set forth and claimed in the claims appended hereto. Those skilled in the medical arts will realize that these principles and/or concepts are capable of being expressed in a variety of forms and/or embodiments. For this reason, this invention is not to be construed as being limited to the illustrative embodiment described herein, but is to be construed only in light of the claims.

DETAILED DESCRIPTION OF THE INVENTION

Certain anomalies of or to, or disease states of, vessels, arteries and organs associated therewith, are candidates for intra arterial-vessel surgery. Included in this group would be aneurysms, arterial-venous malformation, fistulas, catastrophic trauma of, or neoplastic diseases of organs. In all of these instances, potential rupture, as in aneurysms, or an actual opening in the cardio-vascular network as in fisutlas, malformations and trauma, lend themselves to occlusion of the potential or actual opening in the cardiovascular network. Further, in catastrophic trauma to an organ, or in case of neoplastic infiltration of the organ, a total occlusion of the blood supply to the traumatized site, or to the neoplasmic site is also indicated.

In my prior work, boluses of vulcanized silicone have been introduced to the potential site of a rupture, or to the actual site of a rupture, by injection, via a catheter, needle or the like, of a vulcanizing mixture of a vulcanizable silicone. In order to assist in maintaining the components at their intended site during the vulcanizing process, iron particles were suspended in the components of the vulcanizing mixture prior to injection at the site, and magnetism was utilized to maintain the mixture in position for a time sufficient to ensure completion of the vulcanization reaction, as well as thrombosis formation as induced by the iron particles.

Because the iron particles were suspended in the components of the vulcanizable silicone, the particles were dispersed throughout the matrix of the final vulcanized material. Little or no control existed as to location of the particles on the external surface of the final bolus of the vulcanized material. It is, of course, conceivable that all of the iron particles could be included within the interior of the final vulcanized mass, with none of the projecting through the external skin of that vulcanized mass. As such, the thrombosis reaction produced by these iron particles would be absent, and upon removal of the magnetic force holding the vulcanized mass in position at the site of vessel occlusion, the potential existed for dislodgement from this site by the fluid forces present within the vessel or the like.

This problem is surmounted in this invention by including on the surface of a preformed medical balloon or the like, sufficient concentration of a metallic thrombosis-producing material to insure that the metallic thrombosis reaction will occur and, upon formation of a thrombosis, capillary and fibroblast infiltration, followed by scar tissue formation, will insure permanent fixation of the balloon or the like at the occlusion site. Since an external magnetic force is not utilized to maintain the balloon or the like at the occlusion site, it is only necessary to include the metallic particles in a very fine layer on the surface of the balloon or other occluding apparatus, and it is not necessary to include the particles within the matrix of the material which constitute the supporting structure of the balloon or other occluding apparatus. While it would not be contraindicated to so include the metallic particles throughout the matrix of the supporting material, as is noted below, in the preferred method of forming the medical balloon or other occluding apparatus, the metallic particles are located only on the surface of the occluding apparatus.

The preferred occluding apparatus presently envisioned is formed as a detachable vascular balloon insertable at the occlusion site by catheter insertion through an appropriate arterial-venous structure. This allows for treatment of certain cerebral vascular anomalies, which are located in positions within the body not normally accessible through normal surgical techniques. Included would be such conditions as a carotid cavernous sinous fistula, caused by a severe head truama or the like. Thus, to insert an appropriate occluding device, it would not be necessary to subject the traumatized patient to intracranial surgery, because the appropriate occluding device could be located at the site of the fistula by introduction through the carotid artery, utilizing a flexible catheter introduced into the artery upstream from the trauma site.

Certain metals are known to produce what can be described as a metallic thrombosis reaction. When exposed to the cardiovascular system, these metals produce an initial thrombosis at the site of the metal. The thrombosis is invaded by capillary formation and fibroblasts and, ultimately, a scar tissue mass forms at the site. Known to produce this reaction are iron, copper, tantalium, and the noble metals, gold, silver and platinum chromium and their derivates including oxides and alloys such a stainless steel. Presently preferred for use as the metallic thrombosis-producing material would be iron or copper. Tantalium has an added advantage of also acting as a contrasting agent for visualization of the occluding apparatus, using arteriograms and the like.

Normally, the metallic particles utilizable in the invention would be preferredly of a site of 5 microns or less. It has been found that metallic particles of this size or less are non-toxic to the body and if they are dislodged from the surface of the occluding apparatus, they ultimately, for the most part, find their way through the circulatory system to the spleen, where they are stored in a non-toxic state. While metallic particles of a larger size could be utilized, because of the lack of toxicity of the 5 microns or less sized particles, it is preferred to utilize this size particles.

While other metals might also produce the metallic thrombosis reaction, the toxicity of these particles in the body must be considered. All of the metals noted above are considered to be non-toxic to the body, and as such, it is presently preferred to utilize metals chosen from this group.

As opposed to earlier procedures, wherein the metallic particles utilized had to be magnetic because of the use of external magnetic sources in holding the vulcanizing material in place of the body, useful metals for this invention, while including magnetically susceptible metals such as iron, also include non-magnetic metals such as copper and the noble metals noted above.

Further, derivitive forms of preferred metals, where possible, can also be utilized. As such, microspheres of carbonyl iron can be used as metallic thrombosis-producing material. Other, similar derivitive forms of known metallic thrombosis-producing materials could similarly be used, given proper consideration to their toxicity.

The presently preferred occluding apparatus would constitute a small balloon formed from an elastomeric material with the appropriate metallic thrombosis-producing material located on its surface. Referring to the Figures, in FIG. 1, a balloon 10 is shown which, as seen in FIG. 2, is formed from a wall 12 surrounding a hollow interior 14. The balloon 10 includes a stem 16 by which the balloon 10 is appropriately manipulated and attached to a catheter for insertion at the site of occlusion. Located on the surface of the wall 12 is a coating of metallic particles 18.

As shown in FIG. 1, the metallic coating 18 extends over most of the surface of the balloon 10 and as such, the metallic thrombosis reaction followed by capillary aund fibroblast infiltration and scar tissue formation, would occur around the majority of the balloon 10 to insure fixedly locating the balloon 10 in a permanent manner at the site of occlusion.

Preferredly, the balloon 10 is formed of a vulcanized silicone. Presently preferred to form the balloon would be a mixture of a silicone elastomer, Dow Corning Medical Grade Silastic 382, and a dilutant therefor, Dow Corning Medical Grade Silicone Liquid 360. Stannous octoate is preferredly used as the catalyst for cross linking the Silastic 382 and Liquid 360. All of these components are FDA approved for use within the body.

While other elastomeric materials could be utilized, consideration must be given as to toxicity and the like of these materials for use on a long term basis within the body. Other such elastomeric materials could be chosen based upon their toxicity for a long term utilization. Natural latex would be included in a preferred group.

Once delivered to its occluding site within the body, the metallic coated balloon 10 can be inflated via its positioning catheter. The fluid inflating media utilized to inflate the balloon 10 could be an inert, inocuous material such as a prevulcanized mixture of the Silastic 382 and Liquid 360 and an appropriate catalyst located therein, or could be some other material, such as a radiopaque material which would assist in visualization of the in-place balloon.

FIG. 3 illustrates final placement of a balloon 10 within an aneurysm 20, which had formed in the surface of artery 22. The balloon 10 has been positioned within the aneurysm 20 and inflated. In FIG. 3, a time period has expired such that the metallic coating 18 on the surface of the balloon 10 has interacted with the body such that the metallic thrombosis reaction has occured, followed by infiltration of capillaries and fibroblasts, with the subsequent formation of a scar tissue means 24 having formed between the interior walls of the aneurysm 20 and the surfaceof the balloon 10 such that the balloon 10 is fixedly held within the interior of the aneurysm 20. When so positioned within the aneurysm 20, the balloon 10 and that portion 26 of the scar tissue mass 24 located within the fluid channel within the artery 22 forms a seal within the interior of the artery 22 to permanently remove the aneurysm 20 from the circulatory system, removing it as a potential site of catastrophic leakage from the artery 22.

In a similar manner, the balloons 10 could be located in appropriate fistulas which represent actual hemorrhagic sites of the arterial-venous system. Furthermore, balloons 10 could be positioned directly within an artery or vein to seal off all downstream portions of the artery or vein as a therapeutic measure to prevent hemorrhage downstream from the occlusion or sealing site, or as a therapeutic measure to deny a blood supply to a neoplasmic growth served by the artery being so occluded.

The balloon 10 of the invention is preformed outside of the body with the metallic coating 18 being introduced onto the surface of the balloon 10 prior to introduction into the body. This alleviates or removes a consideration which had to be taken into account previously when vulcanization was done at the actual occlusion site. The vulcanization reaction, depending upon the amount of catalyst present and the like, is exothermic in nature. In situ vulcanization, previously utilized, had to account for removal of the heat produced by the exothermic vulcanization reaction. It is evident that, at sites such as cerebral aneurysms and the like, production of heat at the site of the aneurysm could be catastrophic if said heat produced during a vulcanization reaction resulted in degradation of the strength of the aneurysmal wall. It is, of course, quite evident that the status of a particular aneurysm could be such that bursting of the aneurysm and an accompanying hemorrhage could be imminent and heat generated in the surrounding area by a vulcanization reaction could be the catastrophic catalyst resulting in rupture of the same and its grave consequences. Furthermore, the environment of the aneurysm, such as within the brain, could be extremely sensitive to in situ production of heat. By preforming the balloon 10 outside of the body, the final elastomeric properties of the balloon 10 can be the dominant consideration, without consideration having to be given to any heat liberated during vulcanization which would occur by in situ formation of a balloon 10 or a corresponding mass of vulcanized silicone as previously practiced.

The balloon 10 is formed such that a small opening 28 is formed in stem 16. Insofar as the balloon 10, including the stem 16, is formed of a elastomeric material, the stem 16 acts as a valve to seal off the opening 28 unless an implement, such as a catheter or the like, is actually physically located within the opening 28. For introduction into the body, a first catheter would be inserted into the opening 28, with the stem 16 physically squeezing down against the outside of the catheter, maintaining the balloon 10 on to the catheter. When the balloon 10 was in its appropriate occlusion site within the body, it would be inflated by passing an appropriate inflating fluid via the catheter to the interior 14 of the balloon 10. During inflation, the stem 16 would fixedly hold the balloon 10 on to the catheter positioned within the opening 28. After inflation is complete, a second catheter is passed coaxially over the first catheter. The second catheter is of a slightly larger diameter than the first catheter, allowing for slipping of the second catheter along the total length of the first catheter. When the second catheter completely encases the first catheter, it butts up against the end of the stem 16. Further movement of the second catheter along the first catheter pushes against the stem 16, squeezing the balloon 10 off of the end of the first catheter, dislodging it from it. After the balloon 10 is pushed off of the first catheter by the second catheter, the elastic force in the stem 16, by virtue of its being formed of elastomeric material, squeezes the stem 16 down tightly, sealing the opening 28 to leakage of the fluid located within the interior 14.

The fluid utilized to fill the balloon 10 could be any one of a number of fluids, including a radiopaque fluid. Further, the fluid utilized to fill the balloon could be an unvulcanized mixture of the elastomer from which the balloon 10 was formed. However, this mixture could be chosen such that the amount of catalyst would be small, and as such, the vulcanizing reaction would be slow, allowing for slow dispersion of the heat generated during vulcanization. Insofar as the vulcanization reaction of the inflation fluid can be controlled, the vulcanization can be done in a manner to minimize heat liberation during polymerization of the fluid utilized to inflate the balloon 10.

Because of the nature of the materials utilized to form the balloon 10, it is possible for the fluid utilized to inflate the balloon 10 to slowly permeate from within the interior 14 of the balloon 10, causing deflating of the same. However, as opposed to prior use of balloons not having the metallic coating disclosed herein, if the balloon should deflate at a later date, sufficient time would have expired for scar tissue formation to occur, and even upon deflation, there would be no danger of loss of the balloon 10 from the site because of its inclusion within an appropriate mass of scar tissue at the occlusion site.

In fact, in the past, the use of balloons not so coated as described in this invention have become dislodged from their site, and have resulted in medical complications to the patients having received the same. By utilization of the metallic coating 18 on the balloon 10, retention of the balloon 10 at its occlusion site is ensured, because of the formation of the scar tissue around the same.

Normally, the thrombosis reaction will occur soon after insertion of the balloon 10 at the occlusion site. This will be followed by the capillary and fibroblast infiltration and formation of the scar tissue within a short period of time. It can be considered that after two or three days time, sufficient scar tissue would have formed around the balloon 10 to maintain the balloon 10 permanently affixed at its occlusion site.

The size of the balloon 10 utilized depends upon the size of the fistula, aneurysm or the like in which the balloon will be used. It is normally considered that a minimum uninflated size of about 1 millimeter would represent the smallest size of balloon utilized, with the maximum size utilized depending upon the site of usage. Upon inflation, minimum balloon size would be about 2 millimeters, and maximum balloon size would extend up to, but not necessarily restricted to, 10 millimeters. Again, the inflated size of the balloon depends upon its site of usage and size of the balloon is not considered critical to this invention.

The balloons can be formed as either spheres or elongated sausage-like elements, again depending upon their site of usage. The wall thickness of the balloon also would be determined depending upon the site of usage. A thinner wall of course would be utilized for a smaller balloon and a smaller occlusion site with a thicker walled balloon necessary for a larger balloon and a larger occlusion site. Determination of the size and shape of the balloon is, of course dependent upon the site of usage of the same.

The balloons are formed as follows. A mixture of the components utilized to form the elastomeric material is made up and a mandrel of an appropriate size is inserted in the mixture and coated. Preferredly, the mandrel is then withdrawn from the mixture and held horizontally in a chuck and slowly rotated, allowing for polymerization of the components to form the elastomer surrounding the mandrel. A balloon of a single coat can be made this way, or multiple coats can be built up by redipping the previous formed balloon again into an elastomeric mixture and allowing slow vulcanization or polymerization to occur as the mandrel is slowly rotated in a horizontal position. Formation of the opening 28 in the stem 16 would occur by having an appropriate waist section formed in the mandrel, allowing for a smaller diameter section to be formed at the stem 16.

After initiation of polymerization on the mandrel, and when polymerization or vulcanization has occured to a sufficient extent that the balloon can be peeled free from the mandrel, the polymer can then be heat treated to finalize the curing of the same. This would be done in a conventional manner, depending upon the exact elastomer utilized to form the balloon 10.

The amounts of the individual components of the final elastomer would be chosen such that the desired elastomeric properties would be obtained. This is considered to be known to those art skilled in elastomers, and the exact mixtures would be chosen to correspond to known properties of the final elastomers. Normally, for the preferred elastomer of this invention, a silicone elastomer, appropriate amounts of the ingredients noted above, the Silastic 382 and Liquid 360, would be mixed together with an appropriate amount of catalyst, allowing for a reasonable cure time as the mandrel was spun within a chuck. Because of the formation of the ballon outside of the body, as opposed to previous in situ vulcanization reactions, the amounts of the components utilized to form the balloon are subject to a wider variation, depending upon the final properties sought for the balloon 10.

The metallic coating 18 can be applied to the ballon 10 in one of several ways. If the balloon 10 is being made out of a single coat, or it is being made out of multiple coats, when the mandrel is removed from the component mixture, the mandrel is then "dusted" with the appropriate metallic material which will be utilized to form the metallic coating 18. The mandrel is then inserted in the chuck and the polymerization reaction is allowed to proceed, with the "dusted" coat of the coating material 18 on the outside surface of the final coat of the components from which the balloon 10 will be formed. Upon completion of the vulcanization or polymerization reaction with the metallic coating located thereon, the balloon 10 can then be heat treated to effect the final cure.

A second method of applying the metallic coating would be to disperse the metallic coating in a separate mixture of the elastomeric components and, after build up of the initial wall 12 of the balloon 10, the final surface of the ballon 10 is obtained by dipping the mandrel into the component mixture having the metallic component suspended therein to form the final coat thereon, followed by rotation and heat treatment as before.

Upon polymerization or complete vulcanization of the components of the balloon 10, the metallic coating will be locked into the polymeric lattice so formed. Upon inflation of the balloon 10 at its occlusion site, expansion of the elastomeric material will separate the individual metallic particles. However, they will still be present in a sufficient concentration to induce the thrombosis and the subsequent scar tissue formation. If any of the metallic particles forming the coating 18 were sloughed off during inflation of the balloon 10, they of course would be deposited in the immediate area wherein the balloon 10 was being inflated and would still serve to initiate the metallic thrombosis response which would insure the subsequent scar tissue formation to permanently affix the balloon 10 at the chosen occlusion site.

I claim:

1. A process of adhering an inflatable medical balloon within a human body which comprises:
   incorporating onto at least the outside surface of said balloon a composition having the property of inducing the formation of thrombosis followed by capillary and fibroblast invasion of the thrombosis and subsequent scar tissue formation, said composition being chosen from the group consisting of iron, copper, tantalum, gold, silver, platinum, chromium and their derivatives;
   locating said balloon having said composition on its surface within said human body;
   maintaining said balloon in a position within said body for a period of time sufficient such that said composition induces said formation of said thrombosis and said capillary and fibroblast invasion and subsequent scar tissue formation in an area within said body adjacent to said position of said balloon.

2. The process of claim 1 wherein:
said composition is chosen from the group consisting of iron, copper and tantalum, and their derivates.

3. The process of claim 1 wherein:
said inflatable balloon is formed from a supple material.

4. The process of claim 3 wherein:
said material comprises an elastomeric material.

5. The process of claim 4 wherein:
said material comprises a vulcanized silicone and latex.

6. The process of claim 5 wherein:
said material comprises a vulcanized silicone.

7. The process of claim 1 wherein:
said composition is present in a particle site range of about 5 microns and smaller.

8. A medical balloon which comprises:
an inflatable balloon formed from an elastomeric material;
a composition present on at least the outside surface of said balloon, said composition chosen from the group consisting of iron, copper, tantalum, gold, silver, platinum, chromium and their derivatives whereby said composition is capable of inducing the formation of thrombosis followed by invasion of capillaries and fibroblasts and subsequent scar tissue formation.

9. The balloon of claim 8 wherein:
said elastomeric material is a silicone elastomer or latex.

10. The balloon of claim 9 wherein:
said composition is chosen from the group consisting of iron, copper and tantalum and their derivates.

11. The balloon of claim 10 wherein:
said composition is iron.

12. The balloon of claim 11 wherein:
said composition is carbonyl iron.

13. The balloon of claim 12 wherein:
said carbonyl iron is present in a particle size of 5 microns or smaller.

14. The balloon of claim 9 wherein:
said material comprises a vulcanized silicone.

* * * * *

UNITED STATES PATENT AND TRADEMARK OFFICE
CERTIFICATE OF CORRECTION

PATENT NO. : 4,638,803
DATED : JANUARY 27, 1987
INVENTOR(S) : ROBERT W. RAND

It is certified that error appears in the above-identified patent and that said Letters Patent is hereby corrected as shown below:

```
Column 1, line 37, "Cerbral" should be --Cerebral--,
Column 2, line 67, "tantalum" should be --tantalium--,
Column 3, line 66, "the" should be --them--, (2nd occurr.)
Column 4, line 59, "site" should be --size--,
Column 5, line 10, "of" should be --in--,
Column 5, line 14, "derivitive" should be --derivative--,
Column 5, line 17, "derivitive" should be --derivative--,
Column 5, line 35, "aund" should be --and--,
Column 6, line 3, "means" should be --mass--,
Column 6, line 5, "surfaceof" should be --surface of--,
Column 8, line 48, "within" should be --in--,
Column 8, line 48, "ballon" should be --balloon--,
Column 10, line 15, "site" should be --size--.
```

Signed and Sealed this

Twenty-ninth Day of December, 1987

Attest:

DONALD J. QUIGG

*Attesting Officer*   *Commissioner of Patents and Trademarks*